US012678289B2

(12) United States Patent
Salito et al.

(10) Patent No.: US 12,678,289 B2
(45) Date of Patent: Jul. 14, 2026

(54) MEDICAL IMPLANT AND RELATED METHODS

(71) Applicant: Orchid Orthopedic Solutions, LLC, Mason, MI (US)

(72) Inventors: Armando Salito, Wohlen (CH); Parimal Bapat, Novi, MI (US); Shilesh Jani, Collierville, TN (US)

(73) Assignee: Orchid Orthopedic Solutions, LLC, Mason, MI (US)

( * ) Notice: Subject to any disclaimer, the term of this patent is extended or adjusted under 35 U.S.C. 154(b) by 569 days.

(21) Appl. No.: 18/185,159

(22) Filed: Mar. 16, 2023

(65) Prior Publication Data

US 2023/0404764 A1 Dec. 21, 2023

Related U.S. Application Data

(60) Provisional application No. 63/351,839, filed on Jun. 14, 2022.

(51) Int. Cl.
*A61F 2/38* (2006.01)

(52) U.S. Cl.
CPC ...... *A61F 2/38* (2013.01); *A61F 2310/00604* (2013.01); *A61F 2310/00616* (2013.01)

(58) Field of Classification Search
CPC ..................... A61F 2/38; A61F 2/3859; A61F 2310/00604; A61F 2310/00616
See application file for complete search history.

(56) References Cited

U.S. PATENT DOCUMENTS

| | | | |
|---|---|---|---|
| 8,556,972 B2 | 10/2013 | Gordon et al. | |
| 10,219,715 B2 | 3/2019 | Fisk | |
| 2004/0241490 A1 | 12/2004 | Finley | |
| 2008/0160193 A1 | 7/2008 | Mitchell | |
| 2016/0317704 A9 * | 11/2016 | Lyngstadaas | ......... A61L 27/025 |
| 2019/0043640 A1 * | 2/2019 | Ganjoo | .............. C03C 17/3417 |
| 2020/0061242 A1 | 2/2020 | Roeder et al. | |

FOREIGN PATENT DOCUMENTS

| | | |
|---|---|---|
| EP | 4173597 A1 | 5/2023 |
| UA | 13893 U | 4/2006 |
| WO | 2018020490 A1 | 2/2018 |

OTHER PUBLICATIONS

Korean Intellectual Property Office, Written Opinion of the International Searching Authority and International Search Report, mailed Sep. 19, 2023.
Chemnitz University of Technology, J. Rahm, W. Glien, E. Kieselstein, K. KreyBig, P. Sommer, E. Auerswald, U. Kremling, "Optimization of the mechanical and tribological properties of ceramic layers for knee arthroplasty", pp. 67-75, Sep. 25-26, 2003, Chemnitz.
W. Winkler-Gniewek, "Biomaterial aspects of plasma-sprayed oxide ceramic wear protection layers", BIOmaterialien 5 (2), 2004, p. 134.
Extended European Search Report for EP23824412.3 dated May 6, 2026, 10 pages.

* cited by examiner

*Primary Examiner* — Javier G Blanco
(74) *Attorney, Agent, or Firm* — Miller Johnson

(57) ABSTRACT

An implant includes a substrate and a coating. The substrate includes a first outer surface. The coating is disposed on the first outer surface. The coating includes eighty percent titanium dioxide and twenty percent aluminum oxide.

7 Claims, 4 Drawing Sheets

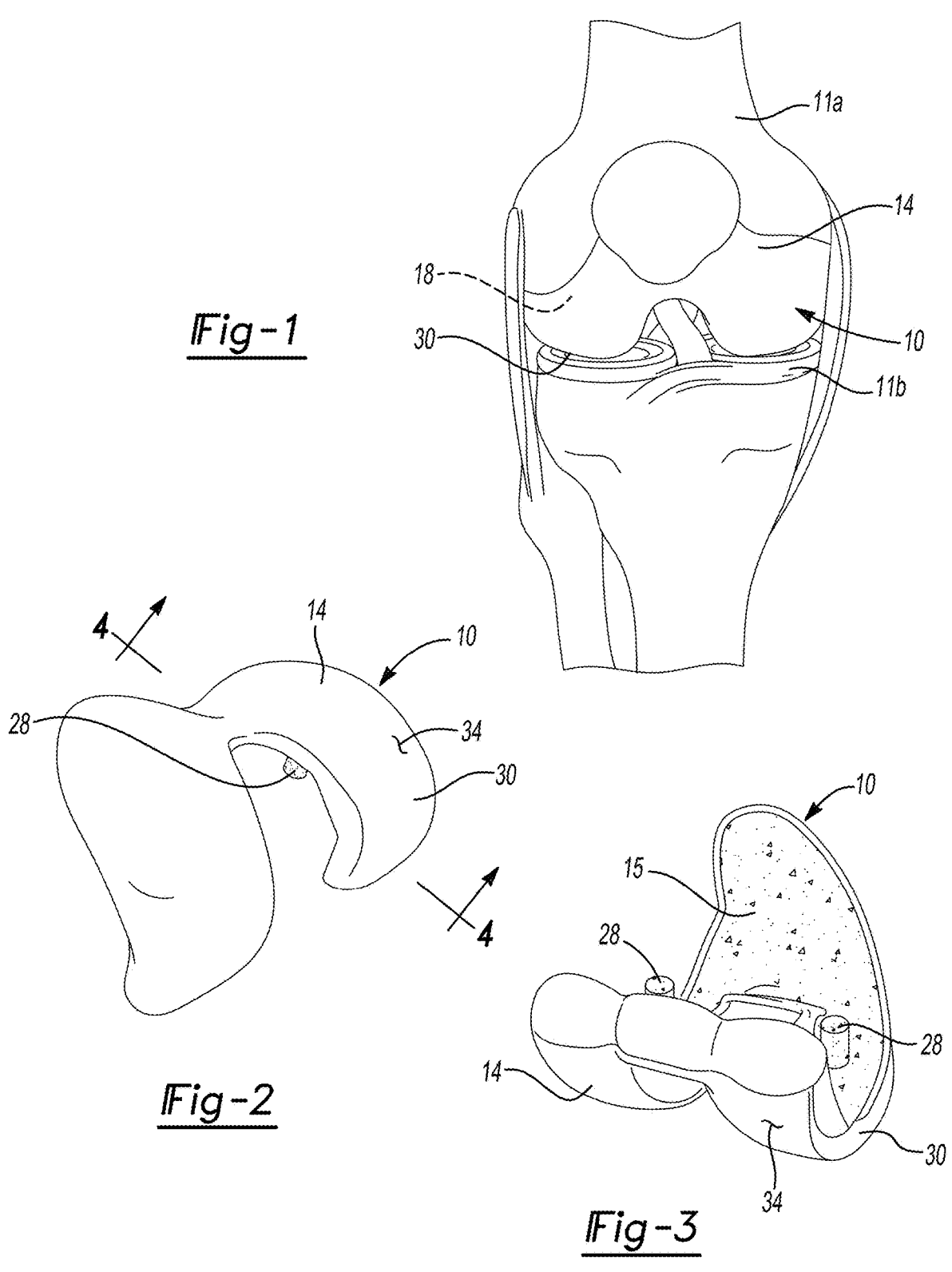
_Fig-1_
_Fig-2_
_Fig-3_

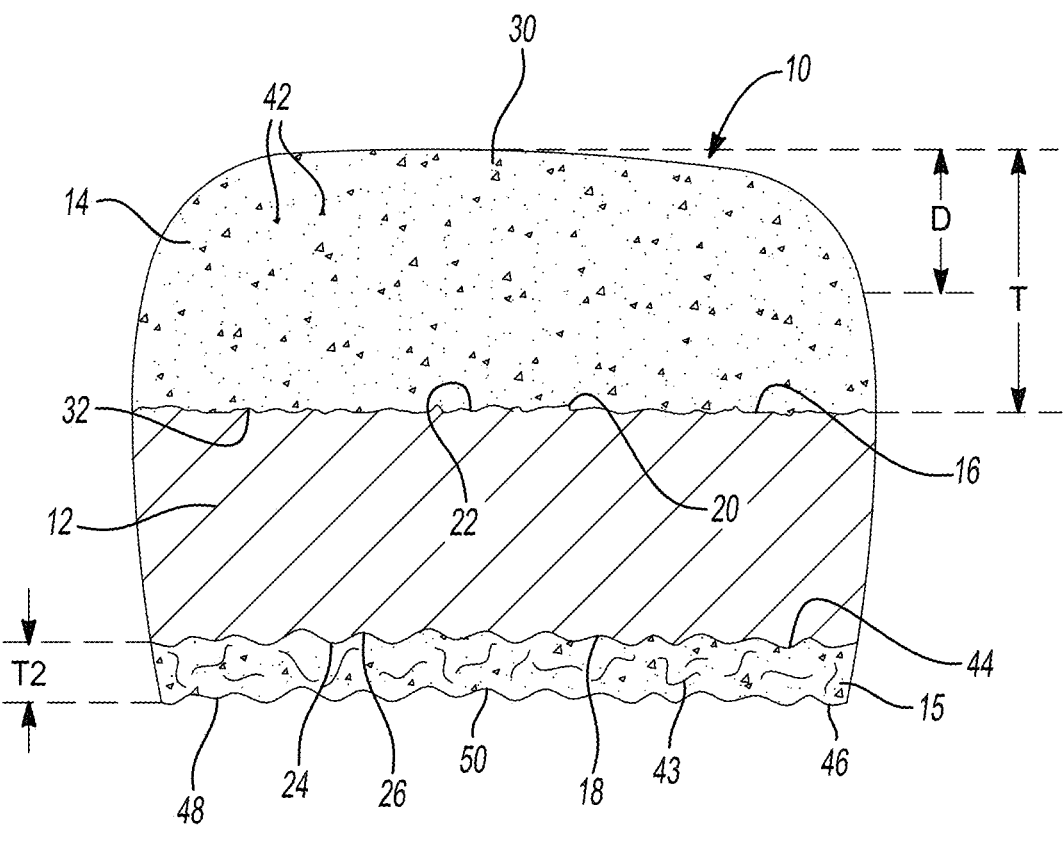
_Fig-4_
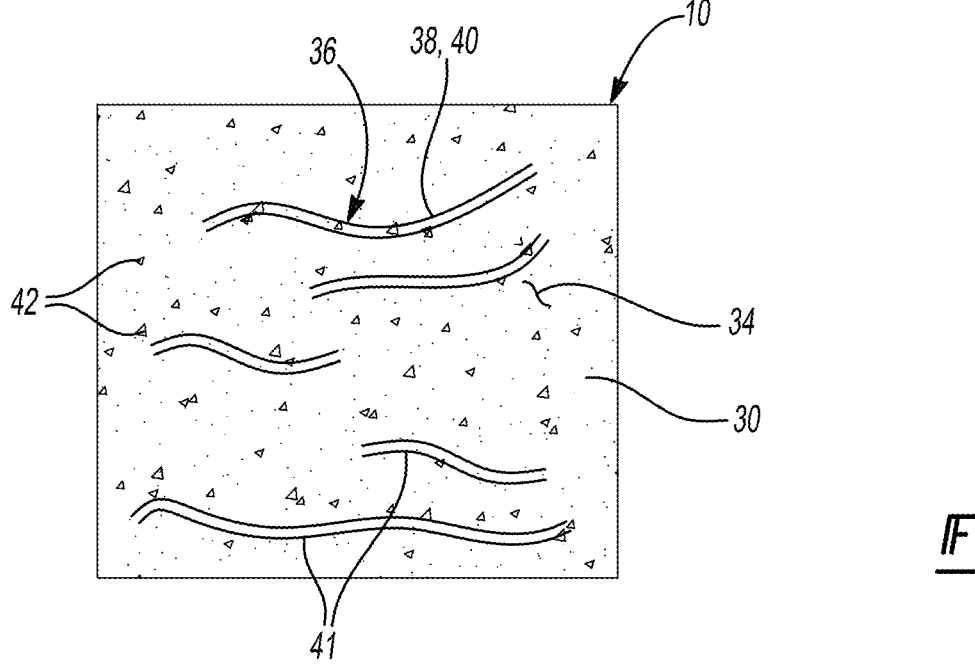
_Fig-5_

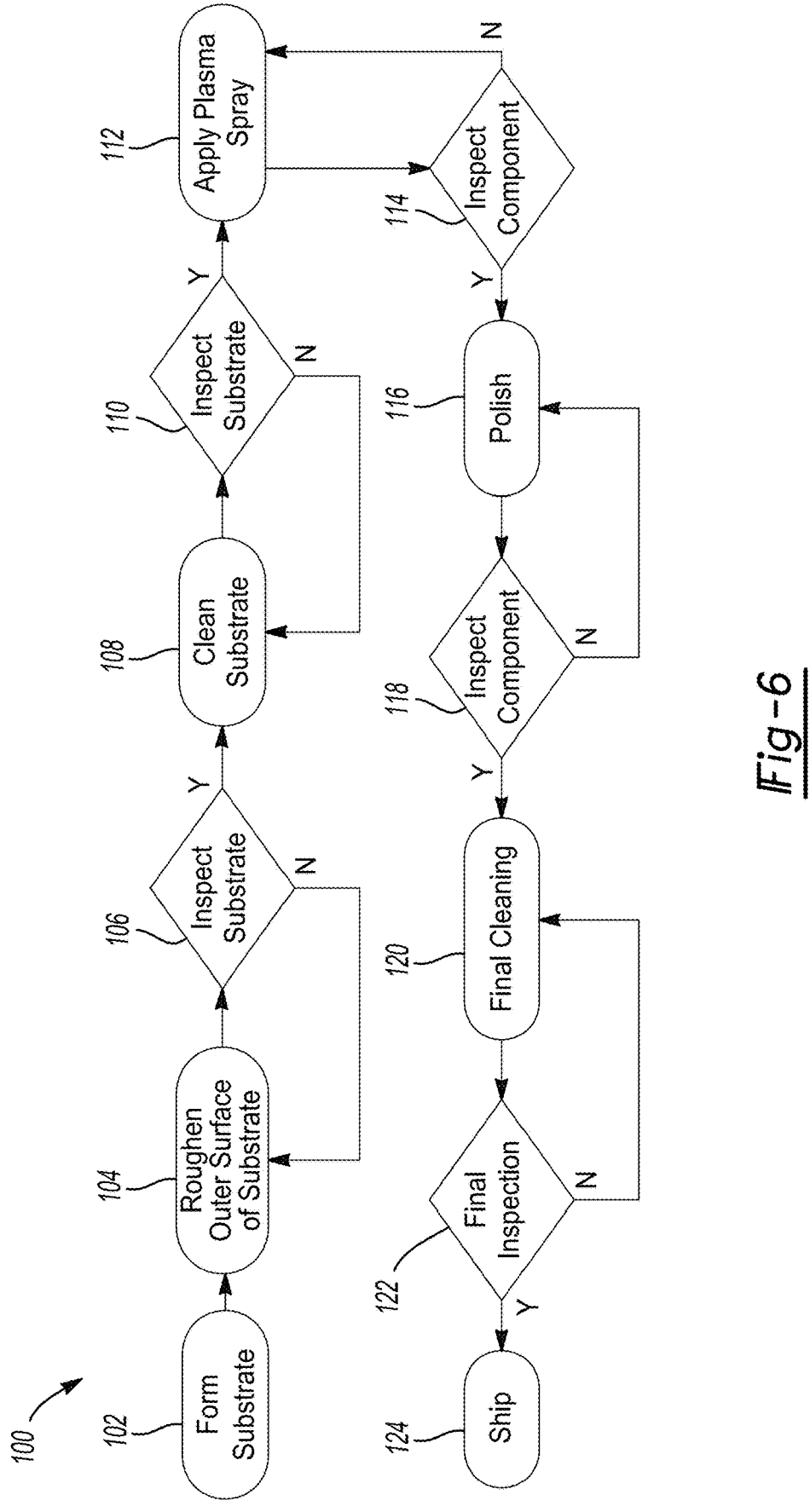
_Fig-6_

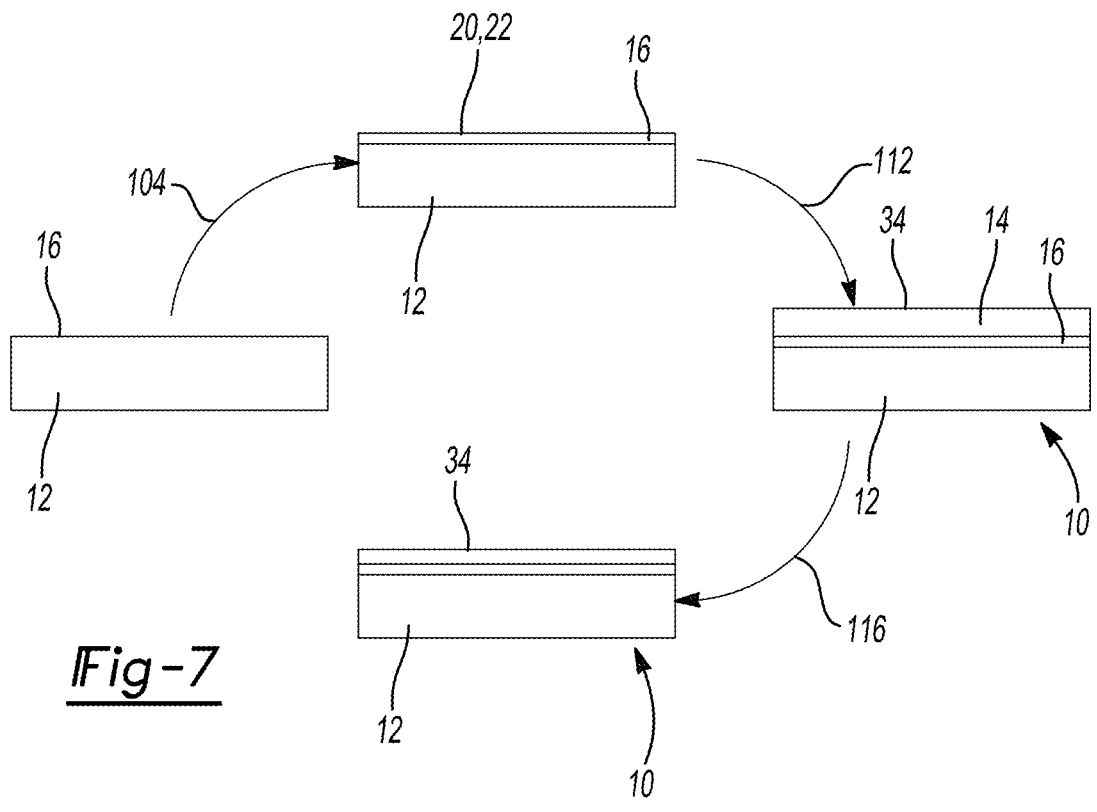
_Fig-7_
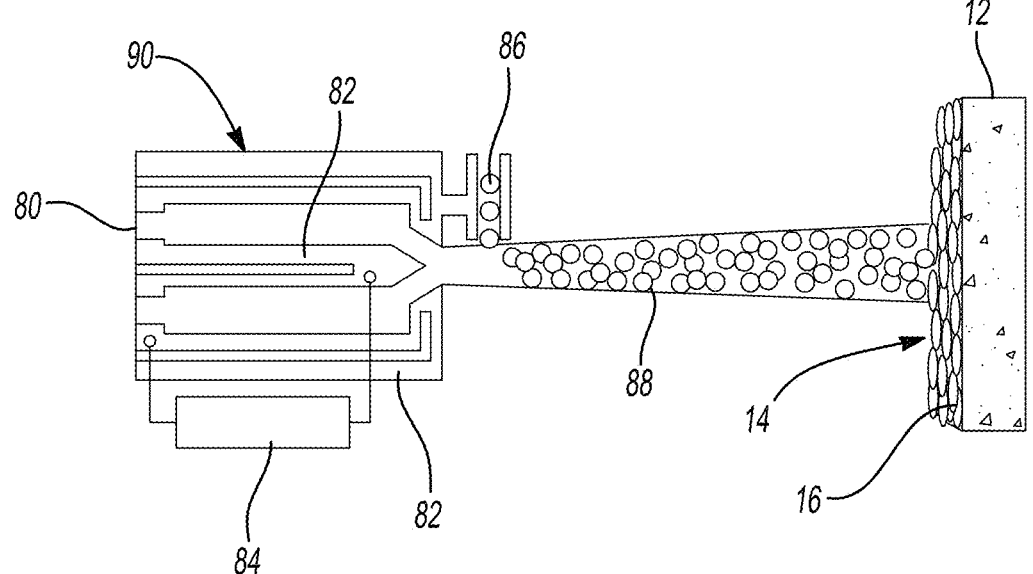
_Fig-8_

MEDICAL IMPLANT AND RELATED METHODS

CROSS-REFERENCE TO RELATED APPLICATIONS

This application claims the benefit of U.S. Provisional Application No. 63/351,839 filed Jun. 14, 2022, the entire disclosure of which is incorporated herein by reference.

TECHNICAL FIELD

This disclosure relates generally to a medical implant, and more particularly to a medical implant including a ceramic coating.

BACKGROUND

This section provides background information related to the present disclosure and is not necessarily prior art. Medical implants are utilized in surgical procedures to repair or replace bones or portions thereof. In some instances, bearing surfaces and/or components of medical implants, such as femoral knee implants, are constructed out of a cobalt chromium alloy (e.g., CoCrMo). Titanium or a titanium alloy (e.g., Ti6AL4V) may be utilized due to superior biocompatibility and an elastic modulus (e.g., stiffness) that is similar to bone. However, titanium alloys also exhibit an inherent softness compared to a harder CoCrMo alloy. Therefore, titanium alloys may undergo a surface hardening process such as application of a coating on an outer surface (e.g., a bearing surface) of the implant substrate. Implant coatings are often applied using a physical vapor deposition process that deposits a coating layer on the outer surface of a substrate. It is known that, as the thickness of a coating layer is increased, certain properties and/or characteristics of the coating layer (e.g., shear strength, tension strength, fatigue strength, etc.) may be reduced. In some implementations, the thickness of the coating layer is less than 10 μm. Over the lifetime of the implant, the coating may be susceptible to delamination, which can expose the underlying implant substrate material (e.g., titanium alloy). While known implants and coatings have proven acceptable for their intended purposes, there remains a continuous need for improvement in the relevant art.

SUMMARY

This section provides a general summary of the disclosure, and is not a comprehensive disclosure of its full scope or all of its features.

One aspect of the disclosure provides an implant. The implant includes a substrate and a coating. The substrate includes a first outer surface. The coating is disposed on the first outer surface. The coating includes eighty percent titanium dioxide and twenty percent aluminum oxide.

Implementations of the disclosure may include one or more of the following optional features. In some implementations, the coating defines a thickness between fifty microns and two hundred microns relative to the first outer surface.

In some implementations, the coating includes a plurality of interstitial voids defining a porosity between two percent and ten percent.

In some implementations, the first outer surface includes a plurality of protrusions. A height of the protrusions may be between two microns and ten microns.

In some implementations, the coating includes a second outer surface defining a first roughness less than 0.1 microns. The second outer surface may define a second roughness greater than 0.1 microns. The substrate may include a distal side defining a third roughness greater than the second roughness.

In some implementations, the coating includes a lamellar pattern. The lamellar pattern may include a plurality of waves formed from (i) an homogenous mixture of aluminum oxide and titanium dioxide or (ii) complex compounds of titanium, aluminum, and oxygen, including complex oxides of titanium and aluminum.

In some implementations, the coating includes a second outer surface. The coating may define (i) an average microhardness greater than seven hundred Vickers between the first outer surface and the second outer surface, (ii) a roughness less than 0.1 microns at the second outer surface, and (iii) a thickness between fifty microns and two hundred microns.

Another aspect of the disclosure provides a method of forming an implant. The method includes forming a substrate including a first outer surface. The method also includes depositing a coating on the first outer surface. The coating may include eighty percent titanium dioxide and twenty percent aluminum oxide.

This aspect may include one or more of the following optional features.

In some implementations, depositing the coating on the first outer surface includes depositing a plurality of layers of the coating on the first outer surface.

In some implementations, forming the substrate includes roughening the first outer surface of the substrate. Forming the substrate may include cleaning the first outer surface.

In some implementations, depositing the coating on the first outer surface includes spraying the coating on the first outer surface. Spraying the coating on the first outer surface may include spraying a plurality of layers of the coating on the first outer surface. Spraying the coating on the first outer surface may include utilizing a thermal plasma spray system.

In some implementations, the coating includes a second outer surface, and the method further comprises polishing the second outer surface to a roughness less than 0.1 microns.

Yet another aspect of the disclosure provides an implant. The implant includes a substrate and a coating material. The substrate includes a first outer surface. The coating material is disposed on the first outer surface. The coating material includes titanium dioxide and aluminum oxide. The coating defines a thickness between fifty microns and four hundred microns relative to the first outer surface.

This aspect may include one or more of the following optional features.

In some implementations, the thickness is between fifty microns and two hundred microns. The thickness may be between fifty microns and one hundred microns.

In some implementations, the coating material includes a plurality of interstitial voids defining a porosity between two percent and ten percent.

In some implementations, the first outer surface includes a plurality of protrusions. A height of the protrusions may be between two microns and ten microns.

In some implementations, the coating material includes a second outer surface defining a first roughness less than 0.1 microns. The second outer surface may define a second roughness greater than 0.1 microns. The substrate may include a distal side defining a third roughness greater than the second roughness.

In some implementations, the coating material includes a lamellar pattern. The lamellar pattern may include a plurality of waves formed from an homogenous mixture of aluminum oxide and titanium dioxide.

In some implementations, the coating includes a second outer surface. The coating may define (i) an average micro-hardness greater than seven hundred Vickers between the first outer surface and the second outer surface, (ii) a roughness less than 0.1 microns at the second outer surface, and (iii) a thickness between fifty microns The details of one or more implementations of the disclosure are set forth in the accompanying drawings and the description below. Other aspects, features, and advantages will be apparent from the description and drawings, and from the claims.

DESCRIPTION OF DRAWINGS

The drawings described herein are for illustrative purposes only of selected configurations and not all possible implementations, and are not intended to limit the scope of the present disclosure.

FIG. 1 is a perspective view of a knee joint comprising an implant according to the principles of the present disclosure FIG. 2 is a top perspective view of an implant according to the principles of the present disclosure.

FIG. 3 is a bottom perspective view of the implant of FIG. 1.

FIG. 4 is a cross-sectional view of the implant of FIG. 1 taken through the line 4-4.

FIG. 5 is a top view of an outer surface of an implant according to the principles of the present disclosure.

FIG. 6 is a flow diagram of an example method of manufacturing an implant according to the principles of the present disclosure.

FIG. 7 is a schematic view of an example method of manufacturing an implant according to the principles of the present disclosure.

FIG. 8 is a schematic cross-sectional view of a plasma vapor deposition system for manufacturing an implant according to the principles of the present disclosure.

Like reference symbols in the various drawings indicate like elements.

DETAILED DESCRIPTION

Example configurations will now be described more fully with reference to the accompanying drawings. Example configurations are provided so that this disclosure will be thorough, and will fully convey the scope of the disclosure to those of ordinary skill in the art. Specific details are set forth such as examples of specific components, devices, and methods, to provide a thorough understanding of configurations of the present disclosure. It will be apparent to those of ordinary skill in the art that specific details need not be employed, that example configurations may be embodied in many different forms, and that the specific details and the example configurations should not be construed to limit the scope of the disclosure.

Referring to FIGS. 1-3, a medical implant 10 is illustrated. As illustrated in FIG. 1, during a medical procedure (e.g., surgery), the implant 10 may be coupled to, and/or replace a portion of, a first bone 11*a* (e.g., a femur) and/or other part (e.g., cartilage) of a human or animal body such that, upon completion of the medical procedure, the implant 10 is coupled to the first bone 11*a* and engages a second bone 11*b* and/or other part (e.g., cartilage) of the human or animal body. In this regard, while the implant 10 is generally shown and described herein as being a femoral knee implant, replacing a portion of the femur and/or cartilage coupled thereto, it will be appreciated that the implant 10 may include, and/or otherwise be utilized in, other applications (e.g., hip, elbow, shoulder, spinal disc, etc.) within the scope of the present disclosure.

With reference to FIGS. 2 and 3, in some implementations, the implant 10 includes a substrate 12 (FIG. 3), a first coating 14, and a second coating 15. As will be explained in more detail below, the first coating 14 may be applied on an outer surface (e.g., an articulating and/or bearing surface) of the substrate 12, and the second coating 15 may be applied on an outer surface (e.g., a bone-contacting surface) of the substrate 12. The substrate 12, the first coating 14, and/or the second coating 16 may be formed at least in part from an anti-thrombogenic, biocompatible material. In this regard, in some implementations, the substrate 12 includes, and/or is formed at least in part from, a metal (e.g., titanium, zirconium, tantalum, etc.) or a metal alloy (e.g., alloys of titanium, zirconium, tantalum, cobalt chromium, stainless steel, etc.). For example, the substrate 12 may include a titanium alloy such as a Ti6AL4V alloy (ASTM F 1472) or a T6$_6$AL4V ELI alloy (ASTM F 136). In some implementations, the substrate 12 includes a plastic such as polyetheretherketone or composite such as a carbon-polyetheretherketone material. While the implant 10 is generally shown and described herein as including the substrate 12, the first coating 14, and the second coating 15, it will be appreciated that the implant may comprise, and/or otherwise be formed entirely from, only the material of the first coating 14 within the scope of the present disclosure.

As illustrated in FIG. 4, the substrate 12 may include a proximal side 16 and a distal side 18 opposite the proximal side 16. In some implementations, the proximal side 16 and/or the distal side 18 collectively and/or individually form an outer surface of the substrate. In this regarding, the proximal side 16 and the distal side 18 may be referred to herein as the "outer surface 16" and the "outer surface 18," respectively.

As will be explained in more detail below, the proximal side 16 may include a rough surface forming a plurality of protrusions 20 and adjacent recesses 22 to which the first coating 14 is attached during a method of manufacturing the implant 10. In this regard, the proximal side 16 may form an interface with the first coating 14 in the manufactured configuration of the implant 10. In some implementations, a height of the protrusions 20 relative to a depth of the recesses 22 is between two microns and ten microns.

The distal side 18 may include a rough surface forming a plurality of protrusions 24 and adjacent recesses 26 to which the second coating 14 is attached during a method of manufacturing the implant 10. In this regard, the distal side 16 may form an interface with the second coating 14 in the manufactured configuration of the implant 10. In some implementations, a height of the protrusions 24 relative to a depth of the recesses 26 is between two microns and ten microns.

The substrate 12 may further include one or more projections 28 extending from the distal side 18. During a medical procedure, the projections 28 may be inserted into apertures (not shown) formed in a part of the body (e.g., first bone 11*a*) to secure the implant 10 to such part of the body. In some implementations, the projections 28 form a cylindrical construct extending from the distal side 18. It will be appreciated, however, that the projections 28 may form other shapes within the scope of the present disclosure.

The first coating 14 may be formed from a material exhibiting antimicrobial properties. In some implementations, the first coating 14 includes a ceramic material. For example, the first coating 14 may include, and/or be formed at least in part from, a mixture of titanium dioxide (i.e., TiO$_2$) and aluminum oxide (i.e., Al$_2$O$_3$). In particular, the first coating 14 may include more than 50% titanium dioxide and less than 50% aluminum oxide. In some implementations, the first coating 14 includes between 70% and 90% titanium dioxide and between 10% and 30% aluminum oxide. In some implementations, the first coating 14 includes between 75% and 85% titanium dioxide and between 15% and 25% aluminum oxide. In some implementations, the first coating 14 includes 80% titanium dioxide and 20% aluminum oxide. Increasing the percentage of aluminum oxide (e.g., greater than 20%) may increase the hardness of the first coating 14.

The first coating 14 may also include, and/or otherwise be formed from, other ceramics, such as zirconium oxides, carbides, and/or nitrides. As illustrated in FIG. 4, the first coating 14 may define a thickness T1 relative to the proximal side 16 of the substrate 12. The thickness T1 may be measured from, and/or defined relative to, a location on the proximal side 16 extending in a direction transverse (e.g., orthogonal) to the substrate 12 at the location. In some implementations, the thickness T1 is greater than ten microns. In some implementations, the thickness T1 is greater than fifty microns. In some implementations, the thickness T1 is greater than one hundred microns. In some implementations, the thickness T1 is between one hundred microns and three hundred microns. In some implementations, the thickness T1 is between one hundred twenty microns and three hundred microns. In some implementations, the thickness T1 is between one hundred fifty microns and two hundred ninety microns.

As illustrated in FIG. 4, the first coating 14 may include a proximal side 30 and a distal side 32 opposite the proximal side 30. Upon implantation, the proximal side 30 may engage and/or bear on a bone (e.g., second bone 11*b*). In another implementation, the proximal side 30 may engage and/or bear on another artificial, implanted bearing material such as ultrahigh molecular weight polyethylene (UHMWPE) or metal alloy. In this regard, the proximal side 30 may be referred to herein as a "bearing side." The distal side 32 may engage and/or interface with the substrate 12. In this regard, the distal side 32 may be referred to herein as the "substrate side." As will be explained in more detail below, upon formation of the implant, the distal side 32 of the first coating 14 may be bonded to the proximal side 16 of the substrate 12. In particular, the distal side 32 of the first coating 14 may bind to the protrusions 20 and recesses 22 formed on the proximal side 16 of the substrate 12. The proximal side 30 of the first coating 14 may form a bearing surface 34 that engages a part of the body (e.g., second bone 11*b*) upon implantation of the implant 10 in the body. With reference to FIG. 5, the surface 34 of the implant may define a lamellar pattern 36 characterized by a plurality of waves 41 formed from a homogenous mixture of titanium dioxide 38 and aluminum oxide 40.

The first coating 14 (e.g., the surface 34) may further define a plurality of interstitial voids 42. In some implementations, the interstitial voids 42 of the first coating 14 define a porosity greater than 0.1% relative to the area of the surface 34 and/or the volume of the first coating 14. In some implementations, the interstitial voids 42 define a porosity greater than 1%. In some implementations, the interstitial voids 42 define a porosity greater than 1.8%. In some implementations, the interstitial voids 42 define a porosity greater 2%. In some implementations, the porosity defined by the interstitial voids 42 is between 2% and 5%. In some implementations, the porosity defined by the interstitial voids 42 is between 2% and 3%.

The second coating 15 may be formed from a material exhibiting antimicrobial properties. In some implementations, the second coating 15 includes a porous material. For example, the second coating 15 may include, and/or be formed at least in part from, titanium, Ti6AL4V, or any other biocompatible metal, defining a plurality of interstitial voids 43. In some implementations, the interstitial voids 43 of the second coating 15 define a porosity greater than thirty percent relative to the volume of the second coating 15.

As illustrated in FIG. 4, the second coating 15 may define a thickness T2 relative to the distal side 18 of the substrate 12. The thickness T2 may be measured from, and/or defined relative to, a location on the distal side 18 extending in a direction transverse (e.g., orthogonal) to the substrate 12 at the location. In some implementations, the thickness T2 is greater than one hundred microns.

As illustrated in FIG. 4, the second coating 15 may include a proximal side 44 and a distal side 46 opposite the proximal side 44. The distal side 46 may include a rough surface forming a plurality of protrusions 48 and adjacent recesses 50 to which a bone (e.g., first bone 11*a*) attached upon implantation of the implant 10. In some implementations, a height of the protrusions 48 relative to a depth of the recesses 50 is between ten microns and fifty microns.

Upon implantation, the proximal side 44 may engage and/or interface with the substrate 12. In this regard, the proximal side 44 may be referred to herein as a "substrate side." The distal side 46 may engage and/or bear on a bone (e.g., first bone 11*a*). In this regard, the distal side 46 may be referred to herein as the "bone-engaging side." As will be explained in more detail below, upon formation of the implant 10, the proximal side 44 of the second coating 15 may be bonded to the distal side 18, including the projections 28, of the substrate 12. In particular, the proximal side 44 of the second coating 15 may bind to the protrusions 24 and recesses 26 formed on the distal side 18 of the substrate 12. The distal side 46 of the second coating 15 may form an outer surface that engages a part of the body (e.g., first bone 11*a*). For example, the protrusions 48, recesses 50, and/or porous construct of the second coating 15 may allow for growth of the bone 11*a* into the distal side 46 of the second coating 15. The height of the protrusions 48 and the depth of the recesses 50 may be greater than the height of the protrusions 24 and the depth of the recesses 26, respectively.

In static tensile and static shear testing, the coating (e.g., coating 14) having thickness T1 demonstrated an adhesion strength greater than twenty-two megapascals and, particularly, greater than thirty-five megapascals. In addition, the coating having thickness T1 withstood ten million cycles of a twenty-five megapascals shear fatigue load and less than sixty-five milligrams of removed material during abrasion resistance testing (e.g., ASTM F 1978 testing standard). The coating having thickness T1 also evidenced no delamination (e.g., adhesive failure) upon application of a thirty Newton load during scratch testing (e.g., ISO 20502 (2005) testing standard). Table 1 lists various adhesion strength values measured upon performance of the listed tests when a roughness of the surface 34 was less than 0.1 microns and when the thickness T1 of the first coating 14 was between fifty microns and two hundred microns. As used herein, roughness may define a difference between the height of protrusions extending from a surface (e.g., surface 34) and the depth of recesses extending into the surface (e.g., surface 34).

TABLE 1

| Test | Adhesion Strength |
| --- | --- |
| Static Tensile | 24 MPa |
| Static Shear | 31 MPa |
| Shear Fatigue | 10 million cycles at 25 MPa |
| Abrasion Resistance | 19 mg |

In addition, the average microhardness (Vickers) was 687.4 HV, 675.6 HV, and 728.24 HV when measured (e.g., ISO 6507-1 (2018) testing standard) at the surface 34 of the coating (e.g., coating 14), the proximal side 16 of the substrate 12, and a depth D between the surface 34 and the proximal side 16 (e.g., at a location measured in the direction of the thickness T1), respectively, when a roughness of the surface 34 was less than 0.1 microns and when the thickness T1 of the first coating 14 was between fifty microns and two hundred microns. In some implementations, the average microhardness of the first coating 14 is (i) greater than the microhardness of various other titanium and/or cobalt-chromium alloys (e.g., Ti6A14V, CoCrMo, etc.), and (ii) less than the microhardness of a bulk ceramic.

A method 100 of manufacturing an implant (e.g., implant 10) will be described with reference to FIGS. 6-8. At step 102, the method 100 may include forming a substrate (e.g., substrate 12). In some implementations, the method 100 includes forming the substrate 12 by additive manufacturing (e.g., three-dimensional printing), forging, machining, grinding, injection molding, and/or casting at step 102 to include the protrusions 24, recesses 26, and projections 28.

At step 104, the method 100 may include roughening the proximal side 16 of the substrate 12. In some implementations, roughening the proximal side 16 of the substrate 12 at step 104 includes striking the proximal side 16 with a material (e.g., sand blasting), striking the proximal side 16 with a laser beam (e.g., laser ablation), and/or striking the proximal side 16 with a tool (e.g., etching) to produce the plurality of protrusions 20 and recesses 22.

At step 106, the method 100 may include inspecting the substrate 12. For example, the method 100 may include inspecting the protrusions 20, 24 and recesses 22, 26 to determine whether one or more various characteristics thereof are within predetermined specifications. If step 106 is "No" (e.g., characteristic(s) of the substrate 12 are not within predetermined specifications), the method may return to one of steps 102 or 104; otherwise, the method may proceed to step 108.

At step 108, the method 100 may include cleaning the proximal side 16 of the substrate 12. In some implementations, cleaning the proximal side 16 of the substrate at step 106 includes striking the proximal side 16 with a gas (e.g., air), liquid (e.g., water) or solid material (e.g., ice, salt, brush, etc.).

At step 110, the method 100 may include inspecting the substrate 12. For example, the method 100 may include inspecting the protrusions 20, 24 and recesses 22, 26 to determine whether one or more various characteristics thereof are within predetermined specifications. If step 110 is "No" (e.g., characteristic(s) of the substrate 12 are not within predetermined specifications), the method may return to one of steps 102, 104, or 108; otherwise, the method may proceed to step 112.

At step 112, the method 100 may include applying a bonding material to the proximal side 16 of the substrate 12. The bonding material may improve bond strength between the coating 14 and the substrate 12. In some implementations, the bonding material and the coating 14 are formed from the same material. In this regard, the bonding material may be formed from a powder that is melted and applied to the substrate 12 by increasing the enthalpy of the process during such application. For example, by altering a flow rate of a gas mixture (e.g., gas 80) and changing a total power applied to the gas mixture by, for example, a current supply (e.g., direct current supply 84), a thin layer of bonding material may be applied to the substrate 12. Alternatively, the bonding material may be applied to the substrate by using a smaller powder particle size relative to a powder particle size used for coating 14. In this scenario, the bonding material and the coating 14 may be applied to the substrate using the same process parameters described below relative to the coating 14; however, the smaller particles of the bonding material may melt and create a thin, dense bonding materials layer having superior bond strength.

At step 112, the method 100 may include applying a coating (e.g., coating 14) to the substrate 12. In some implementations, step 112 includes applying the first coating 14 to the proximal side 16 of the substrate 12 using a thermal plasma spray process (e.g., atmospheric plasma spray or vacuum plasma spray). For example, with reference to FIG. 8, at step 112, the method 100 may include creating a plasma gas 80. In particular, the method 100 may include mixing gases to form the plasma gas 80. In some implementations, the plasma gas 80 is formed from argon gas, nitrogen gas, and/or helium gas.

At step 112, the method may also include igniting the plasma gas 80. For example, electrodes 82 may be utilized to ignite the plasma gas 80. In particular, the method 100 may include passing an electrical current, produced by a direct current supply 84, through the electrodes 82 to initiate a direct current arc discharge and ionize a gas mixture to create the plasma gas 80. At step 112, the method 100 may further include melting a feedstock 86 (e.g., a powered mixture of titanium dioxide and aluminum oxide) to form a coating material 88. For example, the heated plasma gas 80 may be utilized to melt the feedstock 86 and form the coating material 88. In some implementations, every particle of the powdered feedstock 86 comprises 80% titanium dioxide and 20% aluminum oxide. In some implementations, an average size of each particle of the powdered feedstock 86 is forty-five microns.

At step 112, the method 100 may further include depositing particles of the melted feedstock (e.g., coating material 88) on the proximal side 16 of the substrate 12. For example, the method 100 may include ejecting the coating material 88 from a spray gun 90 onto the roughened proximal side 16 of the substrate 12 to form the first coating 14. In some implementations, the spray gun 90 is mounted on a robotic arm (not shown) of a plasma vapor deposition system to provide better control over the deposition step (e.g., step 112).

In some implementations, step 112 includes forming multiple layers of the coating material 88 onto the proximal side 16 of the substrate 12 to obtain a predetermined thickness (e.g., thickness T1) of the first coating 14. In particular, step 112 may be repeated one or more times (e.g., between two times and ten times) to obtain a thickness T1 between fifty microns and three hundred microns. In some implementations, the coating material 88 is deposited at step 112 for a length of time and/or a number of layers until the porosity of the first coating 14 (e.g., the porosity defined by the interstitial voids 42) is greater than 0.1%. In some implementations, the first coating 14 defines a porosity greater than 1%. In some implementations, the coating material 88 is deposited at step 112 for a length of time and/or a number of layers until the porosity of the first coating 14 is greater than 1.8%. In some implementations, the coating material 88 is deposited at step 112 for a length of time and/or a number of layers until the porosity of the first coating 14 is greater 2%. In some implementations, the coating material 88 is deposited at step 112 for a length of time and/or a number of layers until the porosity of the first coating 14 is between 2% and 5%. In some implementations, the coating material 88 is deposited at step 112 for a length of time and/or a number of layers until the porosity of the first coating 14 is between 2% and 3%.

At step 114, the method 100 may include inspecting the substrate 12 and/or coating 14. For example, the method 100 may include inspecting the first coating 14 to determine whether one or more various characteristics (e.g., thickness T1, porosity, roughness, etc.) thereof are within predetermined specifications. If step 114 is "No" (e.g., characteristic(s) of the first coating 14 are not within predetermined specifications), the method may return to one of steps 102, 104, 108, or 112; otherwise, the method may proceed to step 116.

At step 116, the method 100 may including polishing (e.g., smoothing) the outer surface 34 of the first coating 14. For example, the method may include applying and/or striking the outer surface 34 of the first coating 14 with a mechanized belt, liquid, solid, laser, CNC machine, and/or other tool to polish and smooth the outer surface 34. In some implementations, the outer surface 34 of the first coating 14 is polished at step 116 until the surface roughness is between 0.02 microns and ten microns. In some implementations, the method may include polishing the outer surface 34 until the surface roughness is less than 0.1 microns. In some implementations, the method may include polishing the outer surface 34 until the surface roughness is between 0.02 microns and 0.06 microns and/or the thickness T1 is between fifty microns and two hundred microns.

At step 118, the method 100 may include inspecting the substrate 12 and/or coating 14. For example, the method 100 may include inspecting the first coating 14 to determine whether one or more various characteristics (e.g., thickness T1, porosity, roughness, etc.) thereof are within predetermined specifications. If step 118 is "No" (e.g., characteristic(s) of the first coating 14 are not within predetermined specifications), the method may return to one of steps 102, 104, 108, 112, or 116; otherwise, the method may proceed to step 120.

At step 120, the method 100 may include cleaning the first coating 14. For example, the surface 34 of the first coating 14 may be cleaned with a solid, liquid, or gas at step 120.

At step 122, the method 100 may include inspecting the substrate 12 and/or coating 14. For example, the method 100 may include inspecting the first coating 14 to determine whether one or more various characteristics (e.g., thickness T1, porosity, roughness, etc.) thereof are within predetermined specifications. If step 122 is "No" (e.g., characteristic(s) of the first coating 14 are not within predetermined specifications), the method may return to one of steps 102, 104, 108, 112, 116, or 120; otherwise, the method may proceed to step 122 where the method may include shipping the implant 10 to a customer or other destination.

The following Clauses provide an exemplary configuration for in implant and related methods, as described above.

Clause 1: An implant comprising: a substrate including a first outer surface; and a coating disposed on the first outer surface, the coating including eighty percent titanium dioxide and twenty percent aluminum oxide.

Clause 2: The implant of clause 1, wherein the coating defines a thickness between fifty microns and two hundred microns relative to the first outer surface.

Clause 3: The implant of any of clauses 1 through 2, wherein the coating includes a plurality of interstitial voids defining a porosity between two percent and ten percent.

Clause 4: The implant of any of clauses 1 through 3, wherein the first outer surface includes a plurality of protrusions.

Clause 5: The implant of clause 4, wherein a height of the protrusions is between two microns and ten microns.

Clause 6: The implant of any of clauses 1 through 5, wherein the coating includes a second outer surface defining a first roughness less than 0.1 microns.

Clause 7: The implant of clause 6, wherein the second outer surface defines a second roughness greater than 0.1 microns.

Clause 8: The implant of clause 7, wherein the substrate includes a distal side defining a third roughness greater than the second roughness.

Clause 9: The implant of any of clauses 1 through 7, wherein the coating includes a lamellar pattern.

Clause 10: The implant of clause 9, wherein the lamellar pattern includes a plurality of waves formed from an homogenous mixture of aluminum oxide and titanium dioxide.

Clause 11: The implant of any of clauses 1 through 10, wherein coating includes a second outer surface, and wherein the coating defines (i) an average microhardness greater than seven hundred Vickers between the first outer surface and the second outer surface, (ii) a roughness less than 0.1 microns at the second outer surface, and (iii) a thickness between fifty microns and two hundred microns.

Clause 12: A method of forming an implant, the method comprising: forming a substrate including a first outer surface; and depositing a coating on the first outer surface, the coating including eighty percent titanium dioxide and twenty percent aluminum oxide.

Clause 13: The method of clause 12, wherein depositing the coating on the first outer surface includes depositing a plurality of layers of the coating on the first outer surface.

Clause 14: The method of any of clauses 12 through 13, wherein forming the substrate includes roughening the first outer surface of the substrate.

Clause 15: The method of clause 14, wherein forming the substrate includes cleaning the first outer surface.

Clause 16: The method of any of clauses 12 through 15, wherein depositing the coating on the first outer surface includes spraying the coating on the first outer surface.

Clause 17: The method of clause 16, wherein spraying the coating on the first outer surface includes spraying a plurality of layers of the coating on the first outer surface.

Clause 18: The method of any of clauses 16 through 17, wherein spraying the coating on the first outer surface includes utilizing a thermal plasma spray system.

Clause 19: The method of any of clauses 12 through 18, wherein the coating includes a second outer surface, the method further comprising polishing the second outer surface to a roughness less than 0.1 microns.

Clause 20: An implant comprising: a substrate including a first outer surface; and a coating material disposed on the first outer surface, the coating material including titanium dioxide and aluminum oxide and defining a thickness between fifty microns and four hundred microns relative to the first outer surface.

Clause 21: The implant of clause 20, wherein the thickness is between fifty microns and two hundred microns.

Clause 22: The implant of clause 21, wherein the thickness is between fifty microns and one hundred microns.

Clause 23: The implant of any of clauses 20 through 22, wherein the coating material includes a plurality of interstitial voids defining a porosity between two percent and ten percent.

Clause 24: The implant of any of clauses 20 through 23, wherein the first outer surface includes a plurality of protrusions.

Clause 25: The implant of clause 24, wherein a height of the protrusions is between two microns and ten microns.

Clause 26: The implant of any of clauses 20 through 25, wherein the coating material includes a second outer surface defining a first roughness less than 0.1 microns.

Clause 27: The implant of clause 26, wherein the second outer surface defines a second roughness greater than 0.1 microns.

Clause 28: The implant of clause 27, wherein the substrate includes a distal side defining a third roughness greater than the second roughness.

Clause 29: The implant of any of clauses 20 through 27, wherein the coating material includes a lamellar pattern.

Clause 30: The implant of clause 29, wherein the lamellar pattern includes a plurality of waves formed from an homogenous mixture of aluminum oxide and titanium dioxide.

Clause 31: The implant of any of clauses 20 through 30, wherein the coating includes a second outer surface, and wherein the coating defines (i) an average microhardness greater than seven hundred Vickers between the first outer surface and the second outer surface, (ii) a roughness less than 0.1 microns at the second outer surface, and (iii) a thickness between fifty microns and two hundred microns.

The terminology used herein is for the purpose of describing particular exemplary configurations only and is not intended to be limiting. As used herein, the singular articles "a," "an," and "the" may be intended to include the plural forms as well, unless the context clearly indicates otherwise. The terms "comprises," "comprising," "including," and "having," are inclusive and therefore specify the presence of features, steps, operations, elements, and/or components, but do not preclude the presence or addition of one or more other features, steps, operations, elements, components, and/or groups thereof. The method steps, processes, and operations described herein are not to be construed as necessarily requiring their performance in the particular order discussed or illustrated, unless specifically identified as an order of performance. Additional or alternative steps may be employed.

When an element or layer is referred to as being "on," "engaged to," "connected to," "attached to," or "coupled to"

another element or layer, it may be directly on, engaged, connected, attached, or coupled to the other element or layer, or intervening elements or layers may be present. In contrast, when an element is referred to as being "directly on," "directly engaged to," "directly connected to," "directly attached to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

The terms first, second, third, etc. may be used herein to describe various elements, components, regions, layers and/or sections. These elements, components, regions, layers and/or sections should not be limited by these terms. These terms may be only used to distinguish one element, component, region, layer or section from another region, layer or section. Terms such as "first," "second," and other numerical terms do not imply a sequence or order unless clearly indicated by the context. Thus, a first element, component, region, layer or section discussed below could be termed a second element, component, region, layer or section without departing from the teachings of the example configurations.

The foregoing description has been provided for purposes of illustration and description. It is not intended to be exhaustive or to limit the disclosure. Individual elements or features of a particular configuration are generally not limited to that particular configuration, but, where applicable, are interchangeable and can be used in a selected configuration, even if not specifically shown or described. The same may also be varied in many ways. Such variations are not to be regarded as a departure from the disclosure, and all such modifications are intended to be included within the scope of the disclosure.

What is claimed is:

1. An implant comprising:
a substrate including a first outer surface; and
a coating disposed on the first outer surface, the coating including eighty percent titanium dioxide ($TiO_2$) and twenty percent aluminum oxide ($Al_2O_2$),
wherein the coating includes a second outer surface, and wherein the coating defines (i) an average microhardness greater than seven hundred Vickers between the first outer surface and the second outer surface, (ii) a roughness less than 0.1 microns at the second outer surface, and (iii) a thickness greater than fifty microns relative to the first outer surface.

2. The implant of claim 1, wherein the coating includes a plurality of interstitial voids defining a porosity between two percent and ten percent.

3. The implant of claim 1, wherein the first outer surface includes a plurality of protrusions.

4. The implant of claim 1, wherein the coating includes a lamellar pattern.

5. The implant of claim 4, wherein the lamellar pattern includes a plurality of waves formed from an homogenous mixture of the aluminum oxide and the titanium dioxide.

6. The implant of claim 1, wherein the thickness is between fifty microns and three hundred microns relative to the first outer surface.

7. The implant of claim 1, wherein the thickness is between fifty microns and two hundred microns relative to the first outer surface.

* * * * *